(12) United States Patent
Fedorych (10) Patent No.: US 11,698,376 B2
(45) Date of Patent: Jul. 11, 2023

(54) METHOD AND OPTODE FOR DETERMINING THE CONCENTRATION OF AN ANALYTE IN A SAMPLE LIQUID

(71) Applicant: ICHORtec GmbH, Roetgen (DE)

(72) Inventor: Oleh Fedorych, Aachen (DE)

(73) Assignee: ICHORtec GmbH, Roetgen (DE)

( * ) Notice: Subject to any disclaimer, the term of this patent is extended or adjusted under 35 U.S.C. 154(b) by 293 days.

(21) Appl. No.: 16/862,180

(22) Filed: Apr. 29, 2020

(65) Prior Publication Data

US 2021/0164987 A1 Jun. 3, 2021

(51) Int. Cl.
*G01N 33/58* (2006.01)
*G01N 27/327* (2006.01)
*G01N 33/487* (2006.01)
*G01N 21/64* (2006.01)
*G01N 21/77* (2006.01)
(Continued)

(52) U.S. Cl.
CPC ......... *G01N 33/583* (2013.01); *G01N 21/645* (2013.01); *G01N 21/6408* (2013.01);
(Continued)

(58) Field of Classification Search
CPC ............. G01N 33/583; G01N 21/6408; G01N 21/6428; G01N 21/6445; G01N 21/645;
(Continued)

(56) References Cited

U.S. PATENT DOCUMENTS

| 5,246,867 | A |   | 9/1993 | Lakowicz et al. |            |
|-----------|---|---|--------|-----------------|------------|
| 5,626,134 | A | * | 5/1997 | Zuckerman       | G01N 21/6445 |
|           |   |   |        |                 | 356/41     |

(Continued)

FOREIGN PATENT DOCUMENTS

| DE | 102018204744 A1 | 10/2019 |
|----|-----------------|---------|
| DE | 102019132525 B3 | 3/2021  |
| EP | 2805151 B1      | 4/2016  |

OTHER PUBLICATIONS

Hoefelschweiger et al., "Screening scheme based on measurement of fluorescence lifetime in the nanosecond domain", Journal of Biomolecular Screening 10(7); 2005 (Year: 2005).*

(Continued)

*Primary Examiner* — Samuel P Siefke
*Assistant Examiner* — Henry H Nguyen
(74) *Attorney, Agent, or Firm* — Smith, Gambrell & Russell; Judy Jarecki-Black; Ram W. Sabnis (57) ABSTRACT

A method and optode for determining a concentration of an analyte in a sample liquid is provided. The method comprises a radiation source, where excitation radiation is directed onto a carrier unit which is in contact with the sample liquid and has immobilized molecules of a sensor dye that is sensitive to the analyte. The excitation radiation induces luminescence radiation of the sensor dye. This radiation is detected by a radiation detector, which generates an output signal. The analyte concentration is ascertained from the detector output signal using an evaluation routine. This uses a property of the luminescence radiation on the interaction of the concentration of the analyte in the sample liquid used. The dependence of the examined property of the luminescence radiation on an indirect exchange interaction between the individual molecules of the sensor dye, which interact with each other over particles of the analyte.

7 Claims, 4 Drawing Sheets

(51) Int. Cl.
 *G01N 9/24* (2006.01)
 *G01N 15/08* (2006.01)

(52) U.S. Cl.
 CPC ..... *G01N 21/6428* (2013.01); *G01N 21/6445* (2013.01); *G01N 21/77* (2013.01); *G01N 27/327* (2013.01); *G01N 33/487* (2013.01); *G01N 9/24* (2013.01); *G01N 2015/0846* (2013.01); *G01N 2021/6434* (2013.01)

(58) Field of Classification Search
 CPC .... G01N 21/77; G01N 27/327; G01N 33/487; G01N 9/24; G01N 2015/0846; G01N 2021/6434; G01N 2021/6484
 See application file for complete search history.

(56) References Cited

U.S. PATENT DOCUMENTS

| | | | | |
|---|---|---|---|---|
| 6,284,544 | B1 * | 9/2001 | Thompson | G01N 33/582 436/83 |
| 6,395,556 | B1 | 5/2002 | Lakowicz et al. | |
| 2006/0121544 | A1 * | 6/2006 | Boge | G01N 33/542 435/7.92 |
| 2008/0032312 | A1 * | 2/2008 | Amiss | G01N 33/66 435/7.1 |
| 2009/0246888 | A1 * | 10/2009 | Kricka | G01N 33/54333 427/2.13 |
| 2015/0011010 | A1 * | 1/2015 | Steinbrueck | G01N 21/80 422/82.07 |

OTHER PUBLICATIONS

Förster, T., "Experimental and theoretical investigation of the intermolecular transition of electron excitation energy", Journal for Nature Research, 4a: 321-327 (1949). (English Abstract Included).
Förster, T., "Intermolecular Energy Migration and Fluorescence", Annalen der Physik, 437(1-2): 55-75 (1948). (English Abstract Included).

* cited by examiner

METHOD AND OPTODE FOR DETERMINING THE CONCENTRATION OF AN ANALYTE IN A SAMPLE LIQUID

CROSS REFERENCE TO RELATED APPLICATIONS

This application claims benefit of and priority to German Patent Application No. DE10 2019 132 525.0, filed on Nov. 29, 2019 which is incorporated by reference in its entirety.

BACKGROUND

The invention relates to a method for determining the concentration of an analyte in a sample liquid and an optode. The sample liquid can be in particular a biological fluid, such as blood, serum intercellular fluid, cerebrospinal fluid, sweat or urine.

Various methods for the chemical analysis of such liquids are already known, for example flame spectroscopy, photometric methods, colorimetric methods, luminescence methods and methods using ion-selective electrodes or ion-selective optodes. The use of these methods, for example for the analysis of blood samples, requires the extraction of serum or plasma by means of centrifuge, the preparation of a precise volume of the serum sample and the dilution thereof with a precise volume of distilled water.

An optode of the type mentioned at the outset is known from EP 2805 151 B1, by means of which optode the pH or substance concentrations in a sample can be determined using a time-resolved spectroscopy method. It is proposed that a pH-sensitive dye be immobilized in a polymer matrix comprising sulfonated polyether ether ketone (SPEEK). This material allows the pH of the sample to be determined from the decay time of the luminescence of the sensor dye. In the case of materials used for the polymer matrix in the prior art, the interactions between the polymer matrix and the sensor dye led to changes in the optical properties of the sensor dye, which severely restricted its usability for pH determination. In addition to the pH value, other parameters, in particular substance concentrations, can also be determined.

U.S. Pat. No. 5,246,867 discloses a method for measuring the sugar concentration of a sample. For this purpose, a donor-acceptor pair is brought into contact with the sample, with either the molecules of the fluorescent donor or the molecules of the acceptor being immobilized on a carrier material. If a donor binds to an acceptor, this results in a measurable change in the fluorescence lifetime of the donor. The non-immobilized molecules of the donor-acceptor pair compete with the sugar present in the sample, such that, depending on the sugar concentration, the change in the fluorescence lifetime is eliminated or reduced. The change in the fluorescence lifetime is determined using phase-modulated fluorimetry or using time-resolved fluorimetry.

U.S. Pat. No. 6,395,556 B1 discloses a method for determining the concentration of an analyte in a sample liquid, wherein fluorescent sensor molecules are added to the sample liquid, the fluorescence properties of which molecules depend on the concentration of the analyte. Both the sample liquid and a reference liquid having fluorescent reference molecules are exposed to excitation radiation which excite both the reference molecules and the sensor molecules to fluorescence radiation. The fluorescence radiation of the reference liquid is polarized along a first polarization axis and the fluorescence radiation of the sample liquid is polarized along a second polarization axis which is substantially perpendicular to the first. One of the polarized emissions is weakened to such an extent that the intensities on both polarization axes are substantially the same. The analyte concentration can be deduced from the degree of weakening.

A method and an optode of the type mentioned at the outset are known from DE 10 2018 204 744 A1. According to this document, the concentration of analyte ions contained in an electrolyte is determined using a light-irradiated ion-selective membrane that has been immersed in the electrolyte. Reference measurements should not be necessary. A concentration-dependent shift of the spectral position of a luminescence-based absorption, reflection or transmission spectrum of an optode is measured. This method therefore requires the use of an expensive, high resolution spectrometer. The technical problem addressed by the invention is that of providing a method and an optode of the type mentioned at the outset, by means of which reference samples or reference measurements can be largely avoided in a cost-effective manner.

The technical problem is solved by means of a method of the type mentioned at the outset containing the characterizing features in an optode of the type mentioned at the outset containing the characterizing features. Advantageous embodiments are provided.

SUMMARY OF THE INVENTION

The invention is thus based on a method in which, by means of a radiation source, excitation radiation is directed onto a carrier unit which is in contact with the sample liquid and which has immobilized molecules of a sensor dye that is sensitive to the analyte. The excitation radiation induces luminescence radiation of the sensor dye. This radiation is detected by a radiation detector, which generates an output signal. The analyte concentration is ascertained from the detector output signal using an evaluation routine. This uses a property of the luminescence radiation on the interaction of the concentration of the analyte in the sample liquid used. According to the invention, it is now proposed that the dependence of the examined property of the luminescence radiation on an indirect exchange interaction between the individual molecules of the sensor dye, which interact via particles of the analyte, is used to ascertain the analyte concentration. Particles of the analyte can be atoms, ions or molecules.

The exchange interaction, also called exchange energy, is a quantum mechanical phenomenon that occurs when identical particles interact with one another. The exchange interaction is a weak interaction, which in the present context is in the order of meV (millielectron volts) but has a high range. In the case of the indirect exchange interaction, this takes place via the influence of a further variable which is introduced by the particle of the analyte, for example, an electric field in the case of an ionized particle. A sensor dye molecule interacts with a particle of the analyte and this in turn with at least one further sensor dye molecule, which leads to an indirect exchange interaction between at least two molecules of the sensor dye that are involved.

In particular, evaluating a variable that is proportional to the exponential function $$\exp\left(\frac{R}{r - r_0}\right)$$

can be advantageous for the evaluation routine. This dependence is a consequence of the indirect exchange interaction, where R is a measure of the distance between the immobilized molecules of the sensor dye and r is a measure of the distance between the particles of the analyte, which interact with the molecules of the sensor dye. The indirect exchange interaction results when the distance between an involved immobilized molecule of the sensor dye and an analyte particle mediating the exchange interaction is at most r0. r0 is what is known as the Förster radius (Theodor Förster, "*Experimentelle and theoretische Untersuchung des zwischenmolekularen Übergangs von Elektronenanregungsenergie*" [Experimental and theoretical investigation of the intermolecular transition of electron excitation energy], *Zeitschrift für Naturforschung* [Journal for Nature Research], 4a, pp. 321-327 [1949]; T. Förster, *Zwischenmolekulare Energiewanderung and Fluoreszenz* [Intermolecular Energy Migration and Fluorescence], *Annalen der Physik*, Volume 437, Issue 1-2, [1948], pp. 55-75). The indirect exchange interaction becomes relevant if both R<r0 and r<r0 apply.

The aforementioned variables R and r result from the concentration of the immobilized molecules of the sensor dye or the analyte concentration sought.

For a small mass fraction of the immobilized molecules of the sensor dye in the total mass of the carrier unit and sensor dye, the following applies in good approximation:

$$R \approx \frac{1}{(NMN_a)^{\frac{1}{2}}}$$

where N is the molality of the immobilized molecules of the sensor dye based on the carrier unit, M is the density of the carrier unit and Na is the Avogadro number ($\approx 6.022 \cdot 10^{23}$ mol$^{-1}$).

One can find values below 6 mmol/kg may be given for N. For determining salt ions Na+, a tetramethylammonium salt (e.g. Sodium Green™) can be used as sensor dye, for example.

R is a measure of the average distance between the individual immobilized molecules of the sensor dye and is thus a parameter that is known by the optode, specifically by the specified molality of the molecules of the sensor dye, which molality is based on the mass of the carrier unit. This molality can be specified when the carrier unit is being manufactured.

r0 depends on the type of sensor dye and can be ascertained experimentally or by numerical calculation, for example, and can reach up to 10 nm.

The variable r represents the average distance between the particles of the analyte and, in turn, it applies in good approximation with negligible mass of the analyte in the sample liquid:

$$r \approx \frac{1}{(nmN_a)^{\frac{1}{2}}}$$

where n is the molality of the analyte in the sample liquid and m is the density of the sample liquid. The molality n is a direct measure of the analyte concentration sought.

The method according to the invention can be performed in such a way that luminescence radiation lifetime dependence on analyte concentration is used as the property of the luminescence radiation and the evaluation routine for ascertaining the analyte concentration is based on a known concentration of the sensor dye molecules immobilized in the polymer matrix and a known dependence of the lifetime of the luminescence radiation is based on the sensor dye molecule concentration as well as the analyte concentration.

The method according to the invention can be performed in such a way that proportionality is used for the dependence of the lifetime of the luminescence radiation on the sensor dye molecule concentration and the analyte concentration as follows $$\tau \sim \exp\left(\frac{R}{r - r_0}\right)$$

where $\tau$ is the lifetime of the sensor dye luminescence radiation of the immobilized molecules which interact with the analyte.

Luminescence radiation lifetime can be ascertained using time-resolved measurement or phase modulation.

As an alternative to ascertaining the lifetime of the luminescence radiation, analyte concentration can also be determined using the degree of polarization of the luminescence radiation. For this purpose, the method according to the invention is performed in such a way that the excitation radiation is directed onto the carrier unit in a polarized manner and, from a luminescence radiation of the sensor dye induced by the excitation radiation, intensities $I_\parallel$ and $I^\perp$ of two polarization directions that are substantially mutually perpendicularly are determined and, as the property of the luminescence radiation, the dependence of the degree of polarization $$P = \left|\frac{I_{II} - I_\perp}{I_{II} + I_\perp}\right|$$

on the concentration of the analyte is used.

Advantageously, proportionality dependence $$P \sim \exp\left(\frac{R}{r - r_0}\right)$$

can be used.

This proportionality of the degree of polarization of the aforementioned natural exponential function (e function) results from the above-described indirect exchange interaction of immobilized molecules of the sensor dye via particles of the analyte, which provides an additional effect in the electric field.

Exemplary embodiments of the method according to the invention and of the optode according to the invention are illustrated below with reference to figures. For the sake of simpler linguistic representation, some of the exemplary embodiments listed below concern the determination of the concentration of an analyte of a single type, e.g. cooking salt (NaCl), using a specific sensor dye, e.g. a tetramethylammonium salt (e.g. Sodium Green™). However, it is conceivable for the concentration of a plurality of analytes to be determined simultaneously or in succession. In addition, more than one sensor dye may be used.

FIG. 1A-1D show four exemplary variants of a sensor device, also called an optode, which is suitable for carrying out a time-resolved method for determining the concentration of a chemical substance (analyte) in a sample liquid. The sample liquid can be in the form of a single drop or a plurality of drops. This is preferably a biological sample liquid, such as blood, serum, cerebrospinal fluid, intercellular fluid, sweat, or urine.

DETAILED DESCRIPTION

Insofar as the following description of the figures refers to a sensor element or a sensor sub-element, this element has a carrier unit having immobilized molecules of a sensor dye sensitive to the analyte or is formed from such a carrier unit.

Figure 1A:
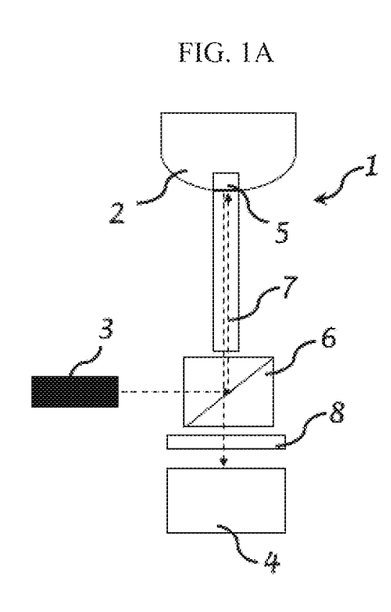
FIG. 1A-1D show four exemplary variants of a sensor device.

A first sensor device 1 has a sample container 2, a pulsed light source 3, e.g. for laser radiation or LED radiation, and a photon counter 4. In the lower region of the sample container 2, preferably inside the sample container 2, a first sensor element 5 is located, the surface of which is intended to come into direct contact with the sample liquid to be analyzed (not shown here). The sensor element 5 has a carrier unit made of a functionalized polymer in which a sensor dye sensitive to the analyte is immobilized and which is hydrogenated when the sample liquid to be analyzed is fed in. The analyte particles penetrate the sensor element 5 such that the sensor dye's immobilized molecules can interact with the analyte particles. The sensor dye immobilized molecules generate a luminescence response to the incident pulsed light, with photons of the luminescence response being guided toward the photon counter 4.

In the case of the first sensor device 1, radiation travels via a beam splitter 6 and an optical fiber 7, which can be a glass fiber, for example. The light originating from the light source 3 is guided via the beam splitter 6 through the optical fiber 7 toward the sensor element 5. Photons originating from the luminescence response arrive at the photon counter 4 via the beam splitter 6. Before entering the photon counter 4, the photons originating from the luminescence response can optionally pass through an optical filter 8, for example a high-pass filter, which is intended to prevent the entry of excitation radiation.

Figure 2:
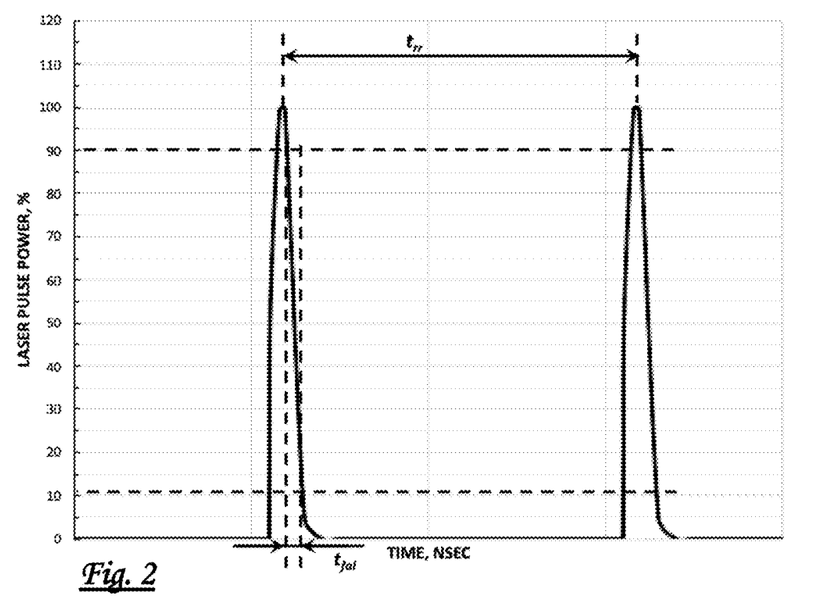
FIG. 2 is a graph showing laser pulse power over time.

The first pulsed light source 3 used emits in the spectral range of the excitation radiation for the molecules of the sensor dye, for example 405 nm or 488 nm. FIG. 2 shows preferred properties of a pulsed light source, as can be used in the first sensor device 1, for example. The spectral range of the excitation radiation is determined by the optical properties of the sensor dye selective places. The decay time tfal of the pulsed light source should be 0.1 ns or shorter. The repetition rate of the pulsed light source should preferably be in the range of megahertz (MHz) or kilohertz (kHz). With a time period trr between two pulses of the light source 3 of 20 ns, the repetition rate 1/trr of the pulsed light source is 50 MHz. A repetition rate of, for example, 50 MHz makes it possible to measure luminescence decay times of down to 20 ns.

The photon counter 4 detects the incoming photons as a function of time. The time resolution of the photon counter 4 should be in the range of 100 ps (0.1 ns) or better. In order to increase the signal-to-noise ratio and to eliminate measurement noise, the measurement can be performed over multiple pulses of the light source 3.

Figure 3:
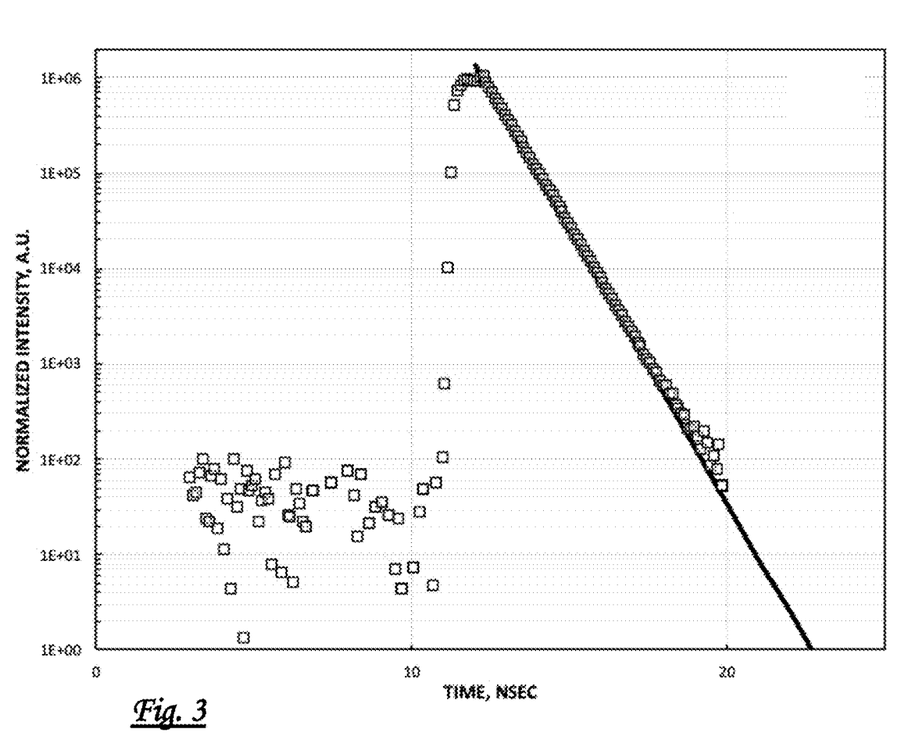
FIG. 3 is a graph showing normalized radiation intensity as ascertained by a photon counter.

FIG. 3 shows the electrical signal generated by the photon counter 4 after amplification and conversion into digital form. The individual measuring points each represent the radiation intensity determined by the photon counter at a particular point in time. For example, laser pulses with a wavelength of 488 nm were produced with the first pulsed light source 3, which leads to a time-dependent fluorescence response.

The graph in FIG. 3, adapted to the measuring points, is a straight line in the logarithmic representation of the graph and shows the time-resolved fluorescence decay, the sensor element 5 of the first sensor device 1 being selective for sodium ions (Na+) as the analyte. The measurement was performed with a known sodium concentration of 15 mmol per liter. The graph was normalized to one million counting pulses and the range of the decay phase was adapted to an exponential decay function.

For the graph, the normalized intensity $$I = I_{max} \exp\left(-\frac{t - t_{delay}}{\tau}\right)$$

where $I_{max}$=1E6, $t_{delay}$=12.2 ns, and $\tau$=0.75 ns, is in the range of the decay phase, where t is the time, $\tau$ is the experimentally ascertained luminescence lifetime, and tdelay is the time delay, dependent on the length of the signal transmission path, between the trigger signal of the power supply for the light source 3 and the signal of the photon counter 4. When the tdelay is known, the luminescence lifetime can therefore be ascertained from the graph adapted to the measuring points.

On the basis of the proportionality $$\tau \approx \tau^* \exp\left(\frac{R}{r - r_0}\right)$$

and the known variables R and r0, the average distance r of the particles of the analyte in the sample liquid and thus the analyte concentration sought can be ascertained.

$\tau$ corresponds to the luminescence lifetime, which is determined from the measured decay of the luminescence according to the formula $$I = I_{max} \exp\left(-\frac{t - t_{delay}}{\tau}\right).$$

R is the average distance between the immobilized molecules of the sensor dye and is specified by the design of the carrier unit, e.g. membrane, which design is provided when the optode is manufactured. r0 is the theoretically calculable or experimentally determinable maximum distance between a particle of the analyte and each participating sensor dye molecule, within which an interaction between the particle of the analyte and the molecules of the sensor dye can occur and an indirect exchange interaction between the involved sensor dye molecules occurs (Förster radius). $\tau^*$ is the increase in the lifetime of the luminescence of the sensor dye caused by the indirect exchange interaction. This parameter can also be calculated theoretically or determined experimentally for each sensor dye (*Zwischenmolekulare Energiewanderung and Fluoreszenz* [Intermolecular energy migration and fluorescence], *Annalen der Physik*, Volume 437, Issue 1-2, [1948], pp. 55-75). A value of $\tau^*=0.6$ ns is obtained for the dependence shown in FIG. 4.

The concentration can thus be determined without a reference measurement.

Figure 4:
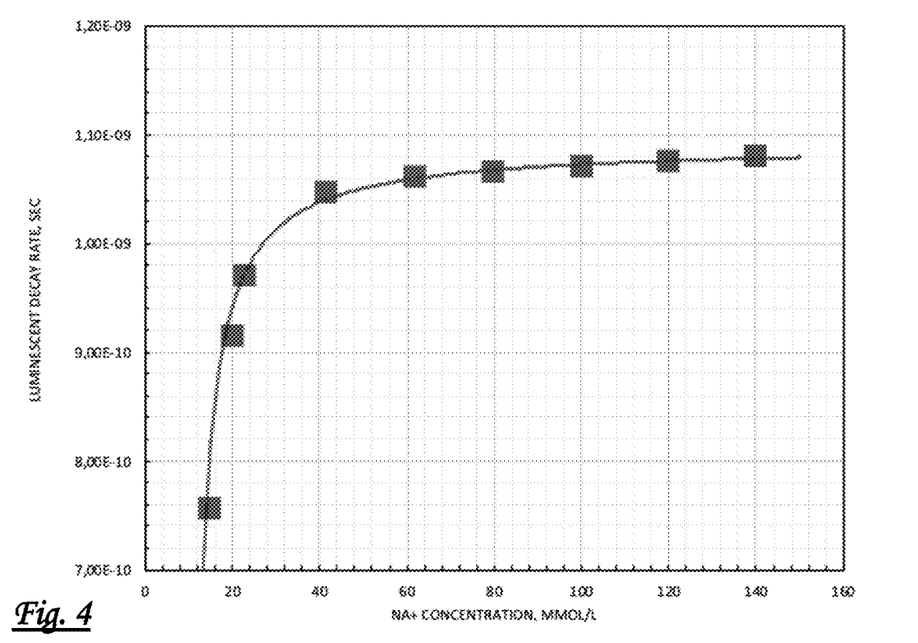
FIG. 4 is a graph showing the luminescent decay rate as a function of the concentration of sodium ions in a tested sample liquid.

FIG. 4 shows the dependence of the concentration of sodium ions in the examined sample liquid on the decay rate of the luminescence. The decay rate is to be understood as an equivalent to the term "lifetime". Using this graph, after a plurality of measurements have been performed in a given sensor device, the concentration of the sodium ions can be ascertained directly from the luminescence lifetime using further measurements.

Figure 1B:
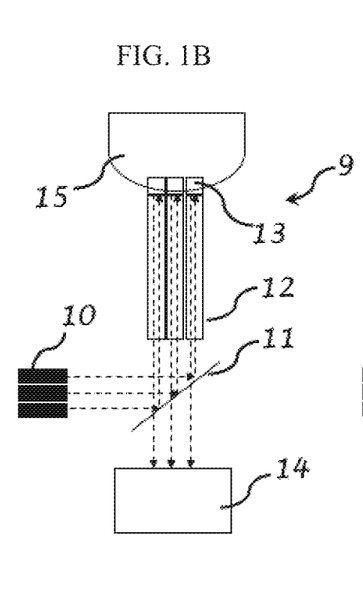

FIG. 1B shows a second sensor device 9, in which a plurality of light beams, generated by a pulsed light source 10, travel via a dichroic mirror 11 and then each via a core of a multi-core optical fiber 12 to a second sensor element 13 arranged in a sample container 15, which element has a plurality of sensor sub-elements. Each sensor sub-element can be provided for a specific analyte, such that the concentrations of multiple analytes can be determined in a sequence of multiple measurements.

The luminescence radiation emanating from the sensor element 13 is guided via the multi-core optical fiber 12 and the dichroic mirror 11 onto a photon counter 14. The dichroic mirror 11 reflects the radiation from the light source, e.g. laser light with a wavelength of 400 to 500 nm, toward the sample and, additionally, allows the luminescence radiation emanating from the sensor element 13 to pass to the photon counter 14.

Figures 1C, 1D:
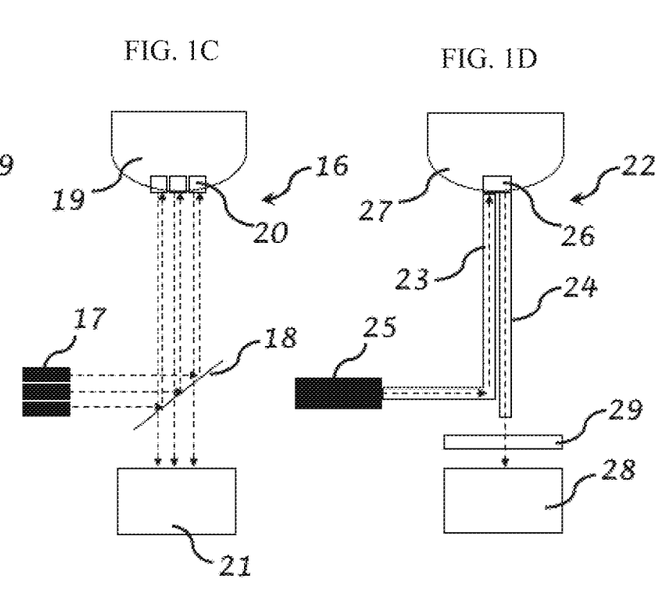

A third sensor device 16 according to FIG. 1C has a similar design to the second sensor device 9 according to FIG. 1B, having a pulsed light source 17, a dichroic mirror 18, a sample container 19, and a sensor element 20 consisting of sensor sub-elements. The multi-core optical fiber 12 of the second sensor device 9 is, however, dispensed with. Instead, the beam is freely guided to the sensor element 20 and, from there, guided to a photon counter 21.

In the variant of a fourth sensor device 22, a first optical fiber 23 guides the radiation generated by a pulsed light source 25 to a fourth sensor element 26 arranged in a sample container 27, and a second optical fiber 24 guides luminescence radiation from the fourth sensor element 26 toward a photon counter 28. Before hitting the fourth photon counter 28, the luminescence radiation passes through an optical filter 29.

In the following, a method utilizing light polarization is presented as an alternative to the time-resolving method.

Figure 5:
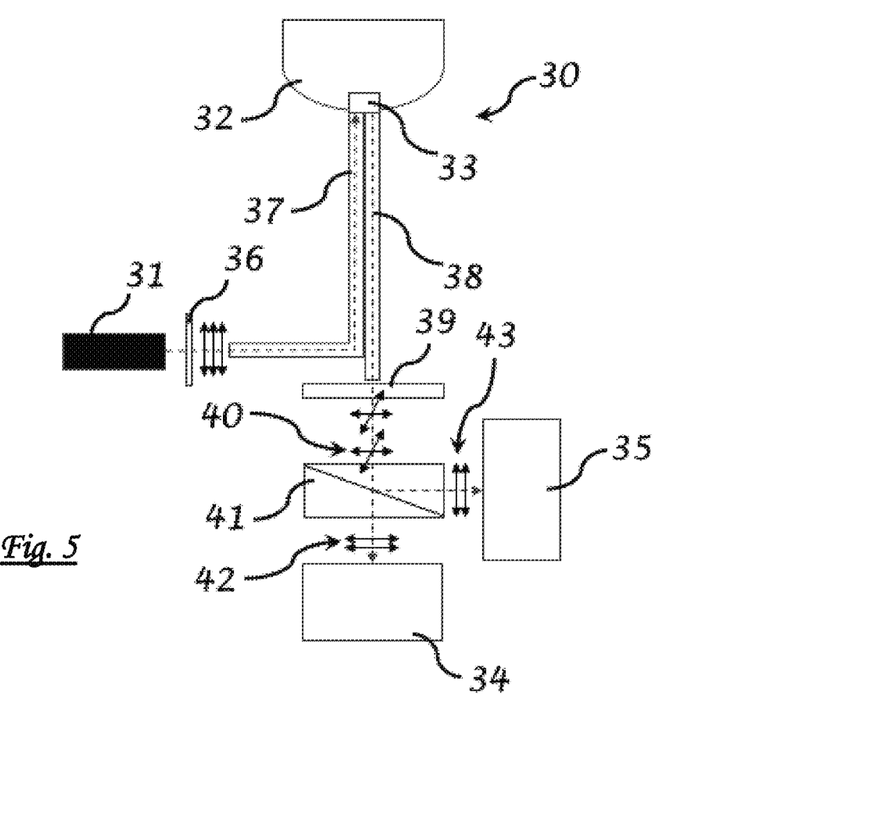
FIG. 5 shows a fifth sensor device with a continuous light source.

FIG. 5 shows a fifth sensor device 30 (optode) with a non-pulsed but continuous light source 31 (e.g. laser or LED), a sensor element 33 arranged in a sample container 32, a first photodetector 34, and a second photodetector 35. After leaving the light source 38, the radiation passes through a linear polarizer 36 to produce linear polarization of the radiation. A first optical fiber 37 then guides the linearly polarized excitation light 40 to the sensor element 33, where it is used for optical excitation. In the sensor element 33 there is a luminescence response to the linearly polarized optical excitation, which response is dependent on the concentration of the analyte.

A captured portion of the luminescence radiation is guided by a second optical fiber 38 toward an optical filter 39, e.g. a high-pass filter, which in particular filters out scattered excitation light. By means of a polarizing beam splitter 41, the incident luminescence radiation is split into two partial beams 42 and 43, which exhibit mutually perpendicular polarizations. The polarization directions are each symbolized by double arrows. The first partial beam 42 strikes the first photodetector 34, and the second partial beam 43 strikes the second photodetector 35. Photodetectors 34 and 35 ascertain the degree of polarization $$P = \left| \frac{I_{\parallel} - I_{\perp}}{I_{\parallel} + I_{\perp}} \right|$$

of the luminescence radiation, where $I\|$ and $I^{\perp}$ represent the intensities of the partial beams having mutually perpendicular polarization directions. The degree of polarization has the proportionality $$P \sim \exp\left(\frac{R}{r - r_0}\right),$$

which is why, from the known variables R and r0 and the relationship between r and the analyte concentration sought (see explanations in the introduction to the description), said concentration can be ascertained.

Figure 6:
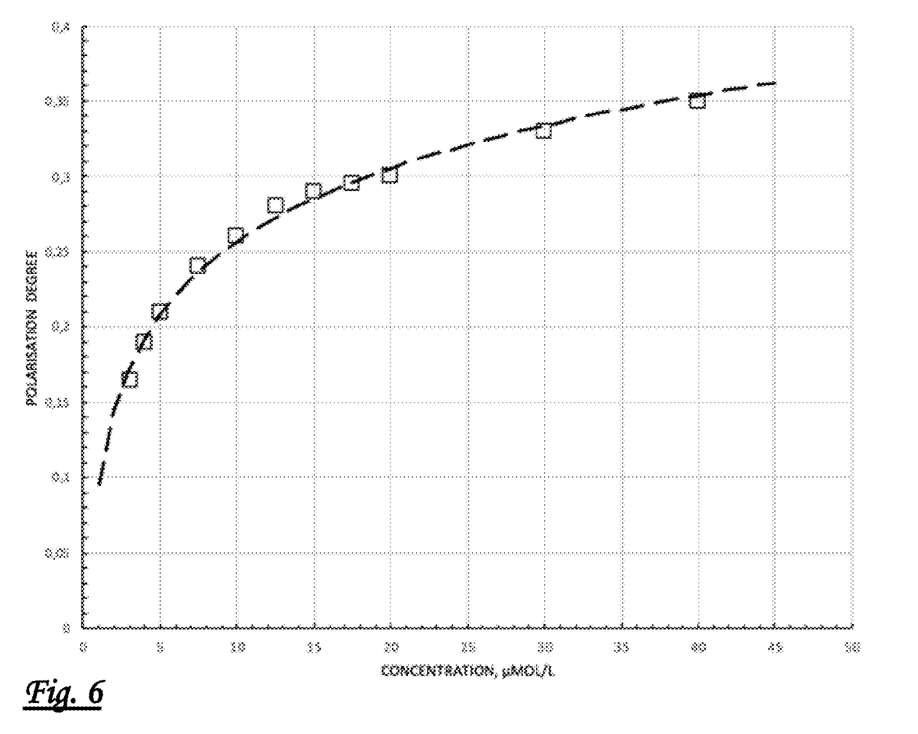
FIG. 6 is a graph showing the degree of polarization of the luminescence radiation as a function of the concentration of the analyte.

FIG. 6 is a graph showing a dependence of the degree of polarization of the luminescence radiation on the concentration of the analyte, the dependence having been ascertained in the aforementioned manner.

Figure 7:
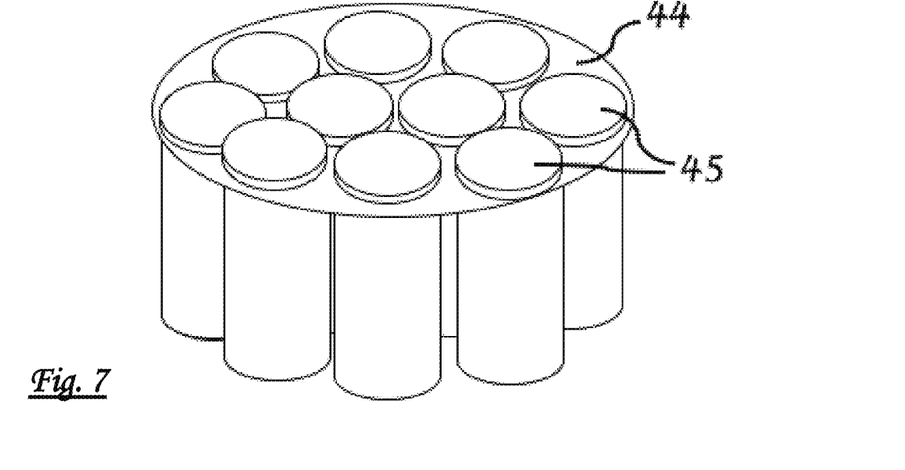
FIG. 7 shows a multi-core optical fiber which has ten core strands.

FIG. 7 shows an example of a multi-core optical fiber 44 having ten core strands 45, each of the strands 45 acting as an independent optical fiber and each ending in a separate sensor element.

| List of reference numerals | |
|---|---|
| 1 | first sensor device |
| 2 | first sample container |
| 3 | first pulsed light source |
| 4 | photon counter |
| 5 | sensor element |
| 6 | beam splitter |
| 7 | optical fiber |
| 8 | first optical filter |
| 9 | second sensor device |
| 10 | second pulsed light source |
| 12 | multi-core optical fiber |
| 13 | second sensor element |
| 14 | photon counter |
| 15 | sample container |
| 16 | third sensor device |
| 17 | third pulsed light source |
| 18 | dichroic mirror |
| 19 | sample container |
| 20 | sensor element |
| 21 | third photon counter |
| 22 | fourth sensor device |
| 23 | optical fiber |
| 24 | optical fiber |
| 25 | fourth pulsed light source |

-continued

| List of reference numerals | |
|---|---|
| 26 | fourth sensor element |
| 27 | sample container |
| 28 | fourth photon counter |
| 29 | optical filter |
| 30 | fifth sensor device |
| 31 | continuous light source |
| 32 | sample container |
| 33 | sensor element |
| 34 | first photodetector |
| 35 | second photodetector |
| 36 | linear polarizer |
| 37 | first optical fiber |
| 38 | second optical fiber |
| 39 | optical filter |
| 40 | linearly polarized excitation light |
| 41 | polarizing beam splitter |
| 42 | first partial beam |
| 43 | second partial beam |
| 44 | multi-core optical fiber |
| 45 | core strand |

What is claimed is:

1. A method for determining a concentration of an analyte in a sample liquid, in which,
a) by means of a radiation source, excitation radiation is directed onto a carrier unit which is in contact with the sample liquid and which has immobilized molecules of a sensor dye that is sensitive to the analyte, wherein the mean distance R between immobilized molecules is smaller than the Förster radius r0,
b) a portion of sensor dye luminescence radiation from which the sensor dye luminescence radiation is induced by the excitation radiation, is applied to a radiation detector in order to generate a detector output signal therefrom, and
c) an evaluation routine ascertains the analyte concentration from the detector output signal, wherein a dependence of an examined property of the luminescence radiation on the concentration of the analyte in the sample liquid is used, characterized in that
d) the dependence of the examined property of the luminescence radiation on an indirect exchange interaction between the individual molecules of the sensor dye is used to ascertain the analyte concentration, wherein the indirect exchange interaction takes place when the molecules of the sensor dye interact with the particles of the analyte, and
characterized in that the evaluation routine evaluates a variable that is proportional to an exponential function $$\exp\left(\frac{R}{r-r_0}\right)$$

where
R is a measure of a distance between the immobilized molecules of the sensor dye,
r is a measure of the distance between the molecules of the analyte that interact with a molecule of the sensor dye, and
r0 is the Förster radius.

2. The method according to claim 1, characterized in that the dependence of a luminescence radiation lifetime on the analyte concentration is used as the property of the luminescence radiation and the evaluation routine for ascertaining the analyte concentration is based on a known concentration of the sensor dye molecules immobilized in a polymer matrix and a known dependence of the lifetime of the luminescence radiation is based on the sensor dye molecule concentration and the analyte concentration.

3. The method according to claim 2, characterized in that, for the dependence of the lifetime of the luminescence radiation on the sensor dye molecule concentration and the analyte concentration, the proportionality $$\tau \sim \exp\left(\frac{R}{r-r_0}\right)$$

is used,
where
$\tau$ is the lifetime of the luminescence radiation of the immobilized molecules of the sensor dye which interact with the particles of the analyte,
R is a measure of a distance between the immobilized molecules of the sensor dye,
r is a measure of the distance between the molecules of the analyte that interact with a molecule of the sensor dye, and
r0 is the Förster radius.

4. The method according to claim 2, characterized in that the lifetime of the luminescence radiation is ascertained by means of time-resolved measurement.

5. The method according to claim 2, characterized in that the lifetime of the luminescence radiation is ascertained by means of phase modulation.

6. The method according to claim 1, characterized in that
a) the excitation radiation is directed onto the carrier unit in a polarized manner and
b) intensities $I_\|$ and $I^\perp$ of sensor dye luminescence radiation, in which the sensor dye luminescence radiation is induced by the excitation radiation, and which intensities are given for two substantially mutually perpendicular polarization directions are determined and, as the property of the luminescence radiation, the degree of polarization $$P = \left|\frac{I_{II} - I_\perp}{I_{II} + I_\perp}\right|$$

on the concentration of the analyte is used,
where
P is polarization degree of the sensor dye luminescence radiation,
$I_\|$ corresponds to the intensity of the sensor dye luminescence radiation polarized in vertical direction or parallel to the polarization direction of the emission source (parallel), and
$I_\perp$ corresponds to the intensity of the sensor dye luminescence radiation polarized in horizontal direction or normal/perpendicular to the polarization direction of the emission source.

7. The method according to claim 6, characterized in that the function $$P \sim \exp\left(\frac{R}{r-r_0}\right),$$

is used, where
P is polarization degree of the sensor dye luminescence radiation,
R is a measure of a distance between the immobilized molecules of the sensor dye,
r is a measure of the distance between the molecules of the analyte that interact with a molecule of the sensor dye, and
r0 is the Förster radius.

* * * * *